(12) United States Patent
Miller

(10) Patent No.: US 7,381,196 B2
(45) Date of Patent: Jun. 3, 2008

(54) VACUUM VENOUS ASSIST CANNULA

(76) Inventor: Nicholas M. Miller, 5708 39th St., Circle E, Bradenton, FL (US) 34203

( * ) Notice: Subject to any disclaimer, the term of this patent is extended or adjusted under 35 U.S.C. 154(b) by 671 days.

(21) Appl. No.: 10/646,330

(22) Filed: Aug. 22, 2003

(65) Prior Publication Data

US 2004/0039370 A1    Feb. 26, 2004

Related U.S. Application Data

(60) Provisional application No. 60/405,801, filed on Aug. 23, 2002.

(51) Int. Cl.
*A61M 1/00*    (2006.01)
(52) U.S. Cl. ............... 604/35; 604/523; 604/93.01
(58) Field of Classification Search ........ 604/523–527, 604/35, 43, 93.01, 541, 6.16, 532, 118; 606/200, 606/108, 191, 198; 239/214.15; 433/91; 15/422
See application file for complete search history.

(56) References Cited

U.S. PATENT DOCUMENTS

| | | | |
|---|---|---|---|
| 3,308,825 A * | 3/1967 | Cruse ..................... 604/267 |
| D250,600 S | 12/1978 | Pick et al. .................... D24/61 |
| 4,129,129 A | 12/1978 | Amrine ...................... 128/214 |
| 4,158,916 A * | 6/1979 | Adler .......................... 433/91 |
| D287,166 S | 12/1986 | Lipsky et al. ................ D24/51 |
| 4,639,252 A | 1/1987 | Kelly et al. .................. 604/282 |
| 4,737,153 A * | 4/1988 | Shimamura et al. ........ 604/526 |
| 5,693,011 A * | 12/1997 | Onik ............................ 604/22 |
| 5,769,828 A * | 6/1998 | Jonkman ..................... 604/526 |
| 5,984,908 A | 11/1999 | Davis et al. ................. 604/282 |
| 6,152,911 A | 11/2000 | Giannoble ................... 604/524 |
| 6,152,912 A | 11/2000 | Jansen et al. ............... 604/526 |

* cited by examiner

*Primary Examiner*—Nicholas D. Lucchesi
*Assistant Examiner*—Laura A Bouchelle

(57) ABSTRACT

A cannula having an elongated tubular flexible body reinforced to prevent kinking in which the distal end of the tube is inserted in the heart and is provided with openings allowing blood to enter the lumen or bore of the tube. A cage structure is located at the tip to maintain the tissue walls of the heart spaced from the openings and prevent obstruction to permit the free flow of blood. In a two-stage cannula, openings also are provided at an intermediate portion of the tubular body spaced slightly from the distal end. This portion also is provided with a cage structure to maintain the openings separated from tissue or organ walls that might otherwise clog the openings.

10 Claims, 3 Drawing Sheets

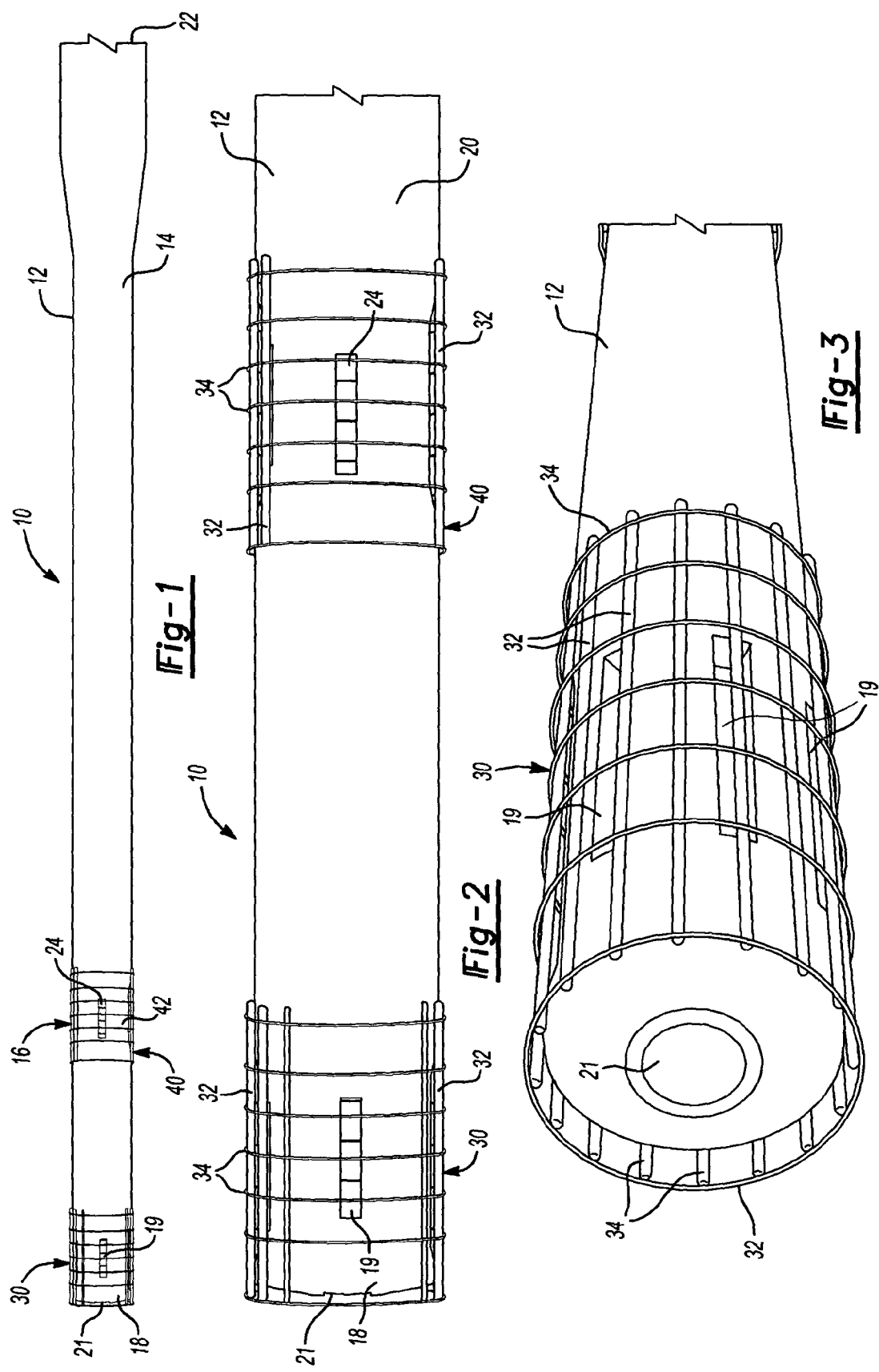

VACUUM VENOUS ASSIST CANNULA

REFERENCE TO RELATED APPLICATION

This application claims priority from U.S. Provisional Patent Application Ser. No. 60/405,801 filed Aug. 23, 2002, the entire content of which is incorporated herein by reference.

FIELD OF THE INVENTION

This invention relates to cannulae or catheters and more particularly to venous return cannulae or catheters used to transport blood away from the heart during open-heart surgery.

BACKGROUND OF THE INVENTION

In open-heart surgery, blood which normally would pass through the heart, is by-passed in a circuit which includes a venous return cannula placed in the heart through an incision in the right atrial appendage. Blood is allowed to drain from the heart to a venous blood reservoir. Differential pressure to insure drainage can be provided by locating the reservoir lower than the heart. In that case, drainage is dependent on the differential created by the position of the heart and the reservoir. A preferred method of insuring and accelerating drainage is to utilize negative pressure or vacuum pressure. By employing vacuum, it is possible to increase blood flow and therefore reduce the internal diameter of the cannula. The reduction in diameter and increase in vacuum pressure differential is limited by the openings in the distal end of the cannula in a single-stage cannula and in the case of a two-stage cannulae, in openings in the distal end and also at an intermediate point spaced slightly from the distal end.

During surgery the openings or intake ports in the cannula must remain completely open without obstruction by tissue or organs coming in contact with the outer surfaces of the cannula to block the intake ports and the flow of blood. The possibility of this occurring increases with an increase in vacuum pressure differential. At the same time, the possibility of decreasing the diameter of the cannula and increasing blood flow is enhanced with an increase in the vacuum pressure differential that might be used.

SUMMARY OF THE INVENTION

There is a need and it is an object of the invention to provide a vacuum venous assist cannula which can have a small internal diameter and can be used with a high vacuum pressure differential without obstructing the blood intake openings or ports in the end of the cannula. Such a device makes it possible to properly install the cannula in the heart through a much smaller incision than normally would be required, which also is highly desirable.

It is another object of the invention to provide a venous cannula that provides a cage or guard structure for preventing obstruction of intake ports of the cannula and wherein such cage structure does not obstruct the insertion and positioning of the cannula during surgery.

A further object of the invention is to provide a vacuum venous assist cannula which increases blood flow to allow a surgeon a bloodless field to perform delicate operations.

The purposes of the invention are attained by a cannula having an elongated tubular flexible body reinforced to prevent kinking in which the distal end of the tube is inserted in the heart and is provided with openings allowing blood to enter the lumen or bore of the tube. A cage structure is located at the tip to maintain the tissue walls of the heart spaced from the openings and prevent obstruction to permit the free flow of blood. In a two-stage cannula, openings also are provided at an intermediate portion of the tubular body spaced slightly from the distal end. This portion also is provided with a cage structure to maintain the openings separated from tissue or organ walls that might otherwise clog the openings.

DESCRIPTION OF THE DRAWINGS

FIG. 1 is an elevation of the two-stage cannula embodying the present invention;

FIG. 2 is an elevation of a portion of the two-stage cannula shown in FIG. 1 and at an enlarged scale;

FIG. 3 is a perspective view of the inlet end of either a two-stage or a single-stage cannula embodying the invention;

DETAILED DESCRIPTION

Figure 5:
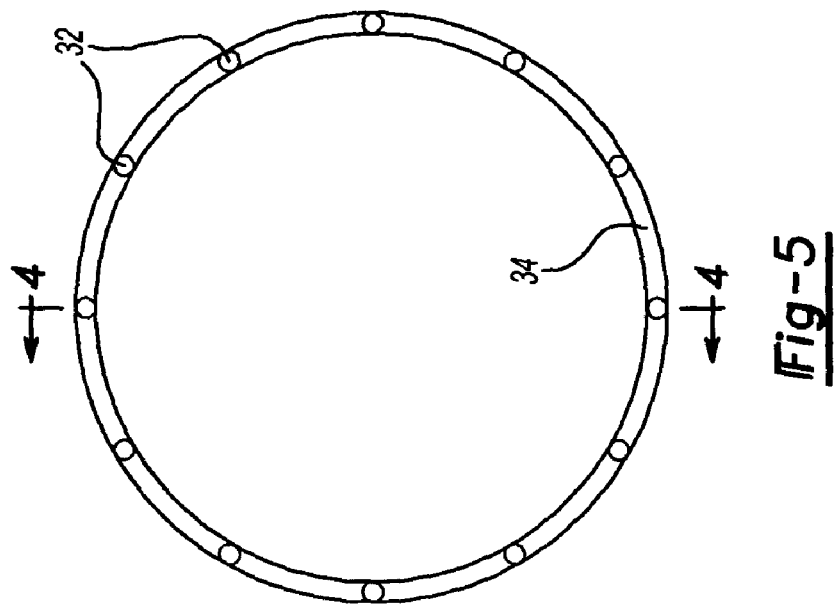
FIG. 5 is a sectional view of the cage portion taken on line 5-5 in FIG. 4.

U.S. Pat. No. 6,152,911 to Giannoble refers to a venous return catheter showing a wire reinforcement to avoid kinking and shows both two-stage and single-stage type of catheters. The patent to Jonkman, U.S. Pat. No. 5,769,828 shows a two-stage venous cannula which is wire reinforced. Both of these patents disclose tubular, wire reinforced structure of the type that can be used with embodiments of the present invention. As these patents demonstrate, the term catheter and cannula appear to be used interchangeably in the prior patented art and it should be understood that the term cannula is used here to identify both of these structures.

Referring to FIG. 1, a two-stage venous cannula, according to the present invention, is designated generally at 10 and is comprised of an elongated and flexible tube 12 of plastic material which is reinforced by helical coils of stainless steel wire 14 that are preformed and imbedded in the plastic tube. The stainless steel coil of wire 14 is substantially continuous except at an intermediate portion 16 of the two-stage cannula 10.

The elongated cannula 10 has an inlet end 18, sometimes called a distal end, which has radially openings or ports 19 to the lumen or bore 20 of the tube 12. The end 18 also has an axial opening 21. The tube 12 has an outlet end 22 from which blood can be exhausted from the bore 20 to an extra-corporeal cardiac bypass system (not shown). A two-stage cannula also has another set of inlet ports 24 formed at the intermediate portion 16 which allows entry of blood from the heart to the bore 18 and exhaust from the outlet end 22 of the cannula.

The two-stage venous return cannula 10 shown in FIG. 1 is positioned in the heart during surgery so that openings or ports 19 and opening 21 in the inlet end 18 are positioned in the inferior venacava for drawing blood therefrom and the inlet ports 24 in the second stage that are spaced from the inlet end 18, draw blood from the right atrium of the heart.

The single-stage cannula has generally the same construction except for the omission of the intermediate portion 14 and the inlet ports 24 associated therewith.

Both the single-stage and two-stage cannula of the present invention are provided with baskets or cages 30 at the inlet end 18. The cages 30 generally are positioned on the exterior of the cannula in the area of the inlet ports and are bonded to the outer surface of the cannula to prevent separation or displacement. The cage element 30 used at the inlet end 18 of both the single-stage and the two-stage cannula shown in FIG. 3 and is made up of a plurality of uniformly and circumferentially spaced longitudinally extending bar elements 32 positioned in direct contact with the outer surface of the tube 12 and a plurality of spaced rings 34 which are fixed in position relative to the bar elements 32 to maintain them in spaced relation.

As seen in FIG. 2, the cage or basket 40 is substantially the same as the cage 30 and is disposed in association with the inlet ports 22 at the intermediate portion 16 of the two-stage cannula. The cages 30 and 40 are constructed in substantially identical fashion. The baskets 30 and 40 can be made of wire coated with plastic or they can be molded of plastic itself, preferably of a quality and characteristics to give a stiffness to both the longitudinal members 32 and the rings 34.

Figure 4:
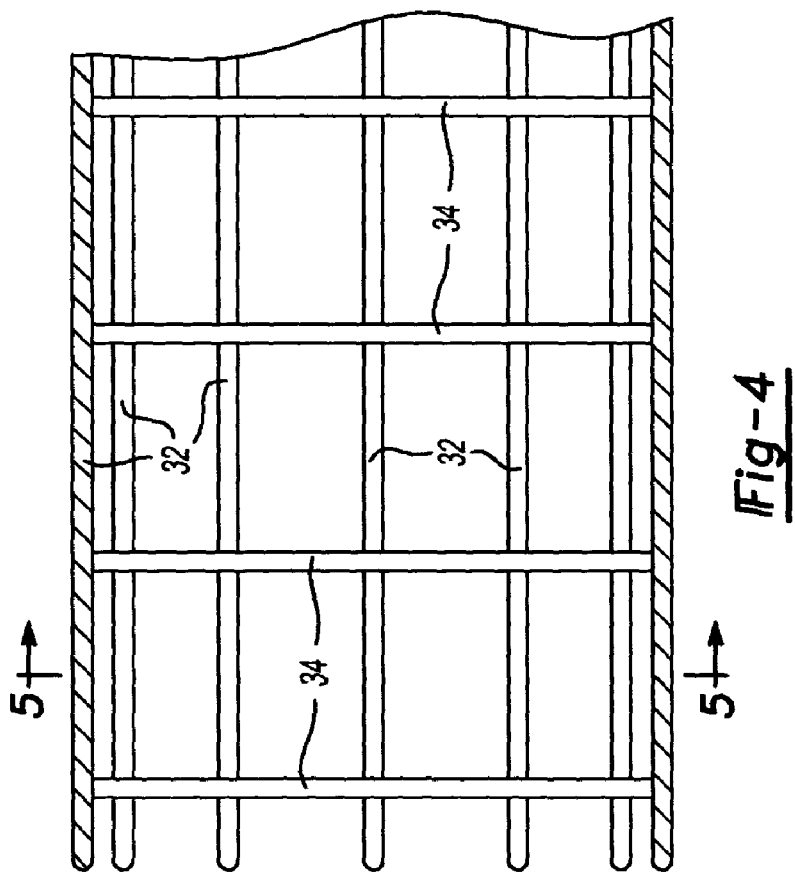
FIG. 4 is a side sectional view taken on line 4-4 in FIG. 5 of one end of the cage element used with the cannula of the present invention and illustrating another embodiment of the invention.

An alternate version of the basket is shown in FIGS. 4 and 5. In this case the basket 30*a* made up of longitudinal bar members 32*a* and rings 34*a* which are disposed in a common cylindrical plane.

Figure 7:
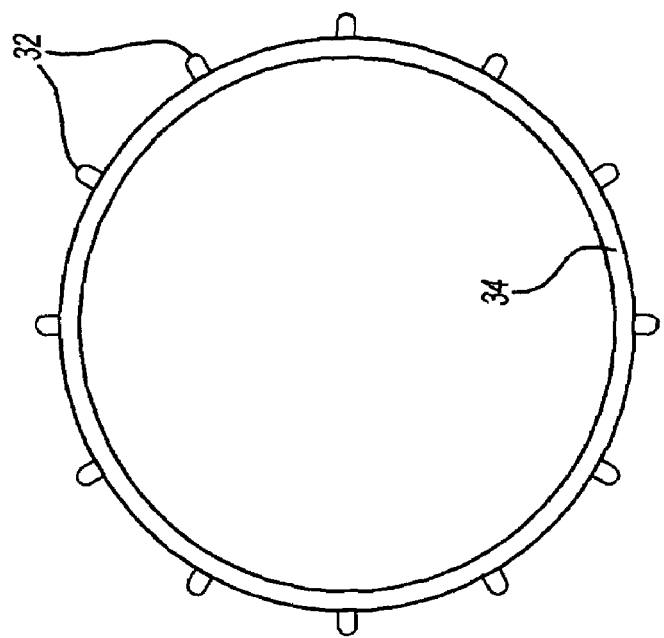
FIG. 7 is an end view of the embodiment of the invention shown in FIG. 6.
Figure 6:
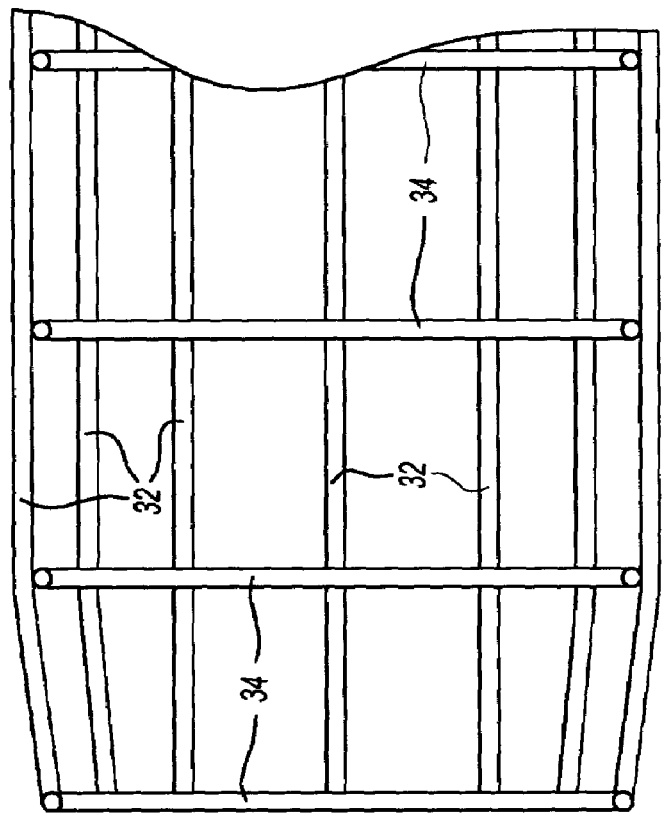
FIG. 6 is a side view of an end portion of a cage element of still another embodiment of the invention.

Still another version of the cage used with the cannula 10 is shown in FIGS. 6 and 7 in which bar members 32*b* are outwardly of the rings 34*b* except at the very left end of the cage 30*b*, as seen in FIG. 6. In that case the bar elements 32*b* are bent slightly to merge in the same plane as the annular ring 34*b*.

In use, the cages serve to prevent tissue of obstructing the inlet openings. When used with a source of vacuum, the pressure differential is sufficiently high so that it is possible for heart tissue to come in contact with the outer surface of a tubular cannula to obstruct blood from entering the inlet ports. The baskets 30, 30*a* and 30*b* are positioned at the inlet end and at the intermediate portion of the cannula in the case of the two-stage cannula, and all act to separate the tissue from the cannula and leave a space for the free flow of blood so that it enters the bore of the cannula and is removed from the heart area.

The invention claimed is:

1. A venous cannula comprising:
   an elongated flexible body member having a tubular wall having an exterior and defining a bore therein and having an intake end and a discharge end;
   a tip portion formed at said intake end and having a plurality of radial openings formed in said wall;
   a rigid helical support element embedded in said tubular wall and extending from said discharge end of said elongated body member to said tip portion; and
   a cage member bonded to the exterior of said wall proximal to said intake end and having a plurality of longitudinally stringers and a plurality of annular rings attached to an outer surface of said plurality of stringers, said cage member being disposed so that all of said plurality of radial openings in said tip portion are covered by said cage member and to maintain adjacent heart tissue walls spaced apart from said plurality of radial openings to permit free flow of blood between the bore and the exterior through said plurality of radial openings.

2. The venous cannula of claim 1 wherein said stringers are stiff relative to said body member.

3. The venous cannula of claim 1 wherein said plurality of stringers are on an outer surface of said tip portion.

4. The venous cannula of claim 1 wherein said plurality of stringers and said plurality of rings are in a common cylindrical plane.

5. The venous cannula of claim 1 wherein said plurality of stringers are on an outer surface of said plurality of rings.

6. The venous cannula of claim 1 wherein additional set of apertures is formed in spaced relation to said tip portion and wherein an additional cage member having rings and stringers is disposed to cover a second set of radial openings.

7. The venous cannula of claim 6 wherein said stringers of said additional cage members are on an outer surface of said tubular wall.

8. The venous cannula of claim 6 wherein said stringers of said additional cage members are stiff relative to said body member.

9. The venous cannula of claim 6 wherein said stringers and said rings are in a common cylindrical plane.

10. The venous cannula of claim 1 wherein said plurality of stringers are uniformly and circumferentially spaced in direct contact with said tubular wall.

\* \* \* \* \*